US010278880B1

(12) United States Patent
Goldman

(10) Patent No.: US 10,278,880 B1
(45) Date of Patent: May 7, 2019

(54) HEAD TREMOR REDUCTION SYSTEM AND METHOD

(71) Applicant: David A. Goldman, Yorktown Heights, NY (US)

(72) Inventor: David A. Goldman, Yorktown Heights, NY (US)

(73) Assignee: Joseph Goldman, New York, NY (US)

( * ) Notice: Subject to any disclaimer, the term of this patent is extended or adjusted under 35 U.S.C. 154(b) by 0 days.

(21) Appl. No.: 16/156,074

(22) Filed: Oct. 10, 2018

(51) Int. Cl.
*A61H 39/04* (2006.01)
*A61H 1/00* (2006.01)
*A61B 5/11* (2006.01)

(52) U.S. Cl.
CPC ............ *A61H 1/008* (2013.01); *A61B 5/1101* (2013.01); *A61H 2201/165* (2013.01); *A61H 2205/027* (2013.01)

(58) Field of Classification Search
CPC .............. A61H 39/04; A61H 2205/024; A61H 2205/028; A61H 2201/1604; A61H 1/008; A61H 2205/02; A61H 2205/027; A61H 2201/165; A61B 5/1101
See application file for complete search history.

(56) References Cited

U.S. PATENT DOCUMENTS

| | | | | | |
|---|---|---|---|---|---|
| 2,482,838 | A | * | 9/1949 | Carlson | A61H 7/002 601/133 |
| 2,664,884 | A | * | 1/1954 | La Verne | A61H 7/002 601/135 |
| 4,479,495 | A | * | 10/1984 | Isaacson | A61F 13/06 606/204 |
| 4,506,659 | A | * | 3/1985 | Chester | A61H 7/006 601/136 |
| 4,920,466 | A | * | 4/1990 | Liu | A61H 23/0263 362/105 |
| 5,115,769 | A | * | 5/1992 | Fiorini | A61H 23/0263 601/71 |
| D328,497 | S | * | 8/1992 | Morrison | D24/200 |
| 5,140,978 | A | * | 8/1992 | Sirninger | A61F 5/01 601/133 |
| 5,421,799 | A | * | 6/1995 | Rabin | A61H 7/006 2/410 |
| 5,468,218 | A | * | 11/1995 | Ward | A61H 7/004 601/101 |
| 5,611,771 | A | * | 3/1997 | Taylor | A61H 23/0263 601/48 |

(Continued)

*Primary Examiner* — Michael J Tsai
*Assistant Examiner* — Christopher E Miller
(74) *Attorney, Agent, or Firm* — Ware, Fressola, Maguire & Barber LLP

(57) ABSTRACT

A head tremor reduction device includes a frame mountable on the head of a person. The frame has two frame arms, each mountable on top of the ear of the person. A mechanical flap pivotably mounted on each of the frame arms to apply a pressuring force on a head area about the rear side of the ear. A section of the frame arm has an arm channel to accommodate a control plate for movement. The control plate has a tapered end portion operatively connected to the mechanical flap to adjust the flap angle in order to change the pressuring force. A control rod slidably engaged in a slot in the frame channel is used for moving the control plate along the arm channel to adjust the flap angle. The frame arm may have a rack movably engaged with a pinion for moving the control plate along the arm channel.

18 Claims, 5 Drawing Sheets

(56) References Cited

U.S. PATENT DOCUMENTS

| | | | |
|---|---|---|---|
| 5,709,647 A * | 1/1998 | Ferber | A61H 39/04 601/134 |
| 6,179,794 B1 * | 1/2001 | Burras | A61H 23/0263 601/46 |
| 6,251,089 B1 | 6/2001 | Kuznets et al. | |
| 6,315,743 B1 * | 11/2001 | Guest | A61H 7/001 601/134 |
| 6,361,549 B1 | 3/2002 | Asatourian et al. | |
| 6,575,923 B1 * | 6/2003 | Burras | A61H 7/001 601/67 |
| 6,638,295 B1 * | 10/2003 | Schroer | A61H 39/04 601/70 |
| 7,300,201 B2 | 11/2007 | Man | |
| 8,353,927 B2 | 1/2013 | Lampropoulos et al. | |
| 9,452,287 B2 | 9/2016 | Rosenbluth et al. | |
| 2002/0080326 A1 * | 6/2002 | Schleger | A61N 2/06 351/121 |
| 2003/0006357 A1 | 1/2003 | Kaiser et al. | |
| 2004/0098037 A1 | 5/2004 | Grey et al. | |
| 2007/0239092 A1 | 10/2007 | Ross | |
| 2008/0039752 A1 | 2/2008 | Rousso | |
| 2009/0177129 A1 | 7/2009 | Chan et al. | |
| 2009/0306561 A1 | 12/2009 | Naganuma | |
| 2011/0139163 A1 * | 6/2011 | Hillila | A61H 23/00 128/861 |
| 2011/0234971 A1 * | 9/2011 | Yeh | A61H 7/001 351/111 |
| 2012/0226095 A1 * | 9/2012 | Young | A61M 21/00 600/15 |
| 2012/0302929 A1 * | 11/2012 | Tkachenko | A61H 23/0254 601/48 |
| 2013/0116606 A1 | 5/2013 | Cordo | |
| 2013/0218197 A1 * | 8/2013 | Tarunni | A61H 39/04 606/204 |
| 2014/0012152 A1 * | 1/2014 | Gentry | A61H 39/02 600/544 |
| 2014/0276279 A1 * | 9/2014 | Li | A61H 39/04 601/136 |
| 2015/0018870 A1 * | 1/2015 | Wardle | A61H 39/04 606/204 |
| 2015/0025569 A1 * | 1/2015 | Wang | A61H 39/04 606/204 |
| 2015/0343189 A1 * | 12/2015 | Ostrovsky | A61N 1/0456 601/46 |
| 2016/0271009 A1 | 9/2016 | Giraud et al. | |
| 2017/0014304 A1 * | 1/2017 | Tarumi | A61H 39/04 |
| 2017/0135896 A1 * | 5/2017 | Snow | A61H 23/0236 |

* cited by examiner

HEAD TREMOR REDUCTION SYSTEM AND METHOD

FIELD OF THE INVENTION

The present invention relates to a head tremor reduction system and, more particularly, to a device that is arranged to apply a pressuring force to the head of a person around the rear of the ear.

BACKGROUND OF THE INVENTION

Traditional tremor control approaches include surgery and medication, with varying success. Surgery also carries risk, and the risk is especially great for operation involving the brain. Medication may have undesirable side effects.

A mechanical device designed to reduce head tremor is advantageous over surgery and medication because it does not have the above-mentioned shortcomings.

SUMMARY OF THE DISCLOSURE

The present invention uses a non-invasive approach to head tremor reduction. It provides a mechanical device to apply flap pressure behind the ear where the ear is connected to the head by cartilage just under the mastoid bone. The flap pressure can be adjusted to suit the reduction need and the comfort to the user. Thus, the first aspect of the presentation is a device for applying pressure to a part of a head of a person, the head having two opposing head sides, each head side including an ear, each ear having a front side and a rear side, said device comprising:

a frame mountable on the head, the frame having two frame arms, each frame arm arranged to contact at least a portion of one of the two head sides;

at least one mechanical flap pivotably mounted on one of the frame arms, the mechanical flap having a flap portion arranged to apply a pressuring force on a head area about the rear side of the ear associated with said of the two head sides; and a movable member configured to cause the mechanical flap to adjust the pressuring force.

According to an embodiment of the present invention, the mechanical flap has a flap angle adjustable to change the pressuring force, and wherein each of the frame arms has a longitudinal axis, and the movable member comprises a control plate movable in a movement direction along the longitudinal axis, the control plate having a plate end portion arranged to contact the mechanical flap for changing the flap angle.

According to an embodiment of the present invention, a section of the frame arm has an arm channel dimensioned to accommodate the control plate for movement along the movement direction, the device further comprising a control member arranged to move the control plate along the movement direction.

According to an embodiment of the present invention, the plate end portion comprises a tapered section to provide a contacting point between the plate end portion and the mechanical flap to form the flap angle.

According to an embodiment of the present invention, the control member comprises a control rod fixedly attached to the control plate, and said section of the frame arm further comprises a slot dimensioned to receive the control rod, the control rod configured to move to different locations in the slot for locating the control plate to different positions in the arm channel so as to change the location of the contacting point between the plate end portion and the mechanical flap.

According to an embodiment of the present invention, the control plate comprises a plate channel dimensioned to mount a rack having a gear bar and a pinion having a gear wheel movably engaged with the gear bar, and the control member comprises a shaft dimensioned to mount the pinion and a disc attached to the shaft, the disc configured to rotate relative to the plate channel so as to move the control plate to different positions in the arm channel for changing the location of the contacting point between the plate end portion and the mechanical flap.

According to an embodiment of the present invention, the section of the frame arm further comprises two mechanical stops separately located in the plate channel to limit movement of the control plate in the arm channel.

According to an embodiment of the present invention, the slot has a slot axis and the control plate has an upper edge and a lower edge, the lower edge has a cant angle relative to the slot axis such that the lower edge of the control plate near the plate end section is lower than the lower edge near the control rod, and wherein the cant angle is between 0 and 15 degrees.

According to an embodiment of the present invention, the flap angle is an angle between the mechanical flap and the head area about the rear side of the ear, and wherein the angle is ranged from 10 to 20 degrees.

According to an embodiment of the present invention, the control plate has one or more slits made thereon near the plate end portion so as to render the control plate flexible near the plate end portion.

According to an embodiment of the present invention, the frame is an eyeglass frame.

The second aspect of the present invention is a method for reducing head tremor of a person, comprising:

providing a frame mountable on a head of said person, the head having two opposing head sides, each head side including an ear, the ear having a front side and a rear side, the frame having two frame arms, each frame arm arranged to contact at least a portion of the head side;

pivotably mounting at least one mechanical flap on one of the frame arms, the mechanical flap having a flap portion arranged to apply a pressuring force on a head area about the rear side of the ear; and providing a movable member to cause the mechanical flap to adjust the pressuring force.

According to an embodiment of the present invention, the mechanical flap has a flap angle adjustable to change the pressuring force and wherein each of the frame arms has a longitudinal axis, and the movable member comprises a control plate movable in a movement direction along the longitudinal axis, the control plate having a plate end portion arranged to contact the mechanical flap to change the flap angle.

According to an embodiment of the present invention, the method further comprises:

providing an arm channel in a section of the frame arm, the arm channel dimensioned to accommodate the control plate for movement along the movement direction; and providing a control member to move the control plate along the movement direction.

According to an embodiment of the present invention, the plate end portion comprises a tapered section to provide a contacting point between the plate end portion and the mechanical flap to form the flap angle.

According to an embodiment of the present invention, the method further comprises:

fixedly attaching a control rod to the control plate, and
providing a slot on said section of the frame, the slot dimensioned to receive the control rod, the control rod configured to move to different locations in the slot for locating the control plate to different positions in the arm channel so as to change the location of the contacting point between the plate end portion and the mechanical flap.

According to an embodiment of the present invention, the method further comprises:

providing a plate channel on the control plate, the plate channel dimensioned to mount a rack having a gear bar and a pinion having a gear wheel movably engaged with the gear bar, and wherein the control member comprises a shaft dimensioned to mount the pinion and a disc attached to the shaft, the disc configured to rotate relative to the plate channel so as to move the control plate to different positions in the arm channel for changing the location of the contacting point between the plate end portion and the mechanical flap; and providing two mechanical stops separately in the plate channel to limit movement of the control plate in the arm channel.

According to an embodiment of the present invention, the slot has a slot axis and the control plate has an upper edge and a lower edge, the lower edge has a cant angle relative to the slot axis such that the lower edge of the control plate near the plate end section is lower than the lower edge near the control rod, and wherein the cant angle is between 0 and 15 degrees.

According to an embodiment of the present invention, the flap angle is an angle between the mechanical flap and the head area about the rear side of the ear, and wherein the angle is ranged from 10 to 20 degrees.

BRIEF DESCRIPTION OF THE DRAWINGS

FIG. 5 shows a cross sectional view of the frame arm of FIG. 4a.

DETAILED DESCRIPTION OF THE INVENTION

Figure 1:
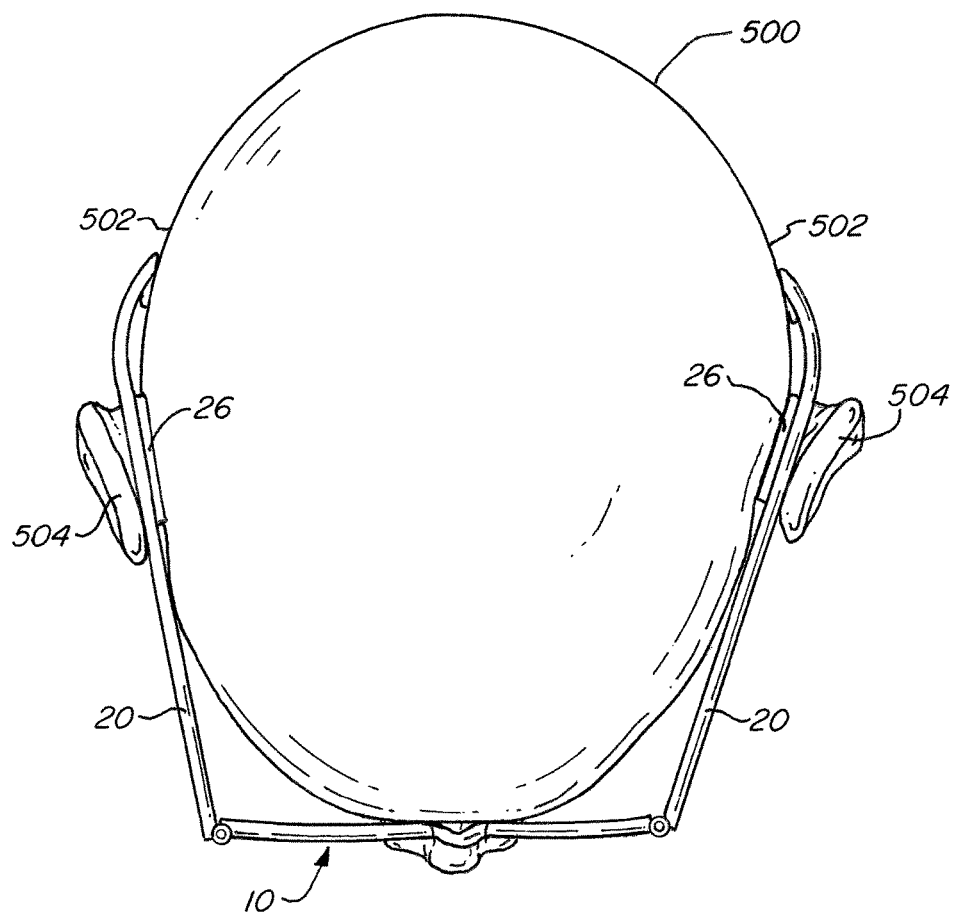
FIG. 1 illustrates a top view of the head of a person wearing a head-tremor reduction frame, according to an embodiment of the present invention.

The present invention provides a head tremor reduction device in the form of a frame, similar to an eyeglass frame. The frame 10 can be put on the head of a person. The frame has two frame arms 20 to be placed on the top of the ears. Each frame arm 20 has an independently adjustable tremor reduction mechanism 29. The tremor reduction mechanism 29 includes a mechanical flap 26, which is pivotably mounted on each of the frame arms 20 to apply a pressuring force behind each of the ears where the ear is connected to the head by cartilage just under the mastoid bone. The tremor reduction mechanism 29 also has a control section 36 operatively connected to the mechanical flap 26 for controlling the flap angle. The head tremor reduction mechanism 29 can also be implemented on the frame of a pair of eyeglasses. Using eyeglasses to implement the head tremor reduction mechanism 29 is advantageous in that the mechanism is unobtrusive. Furthermore, as the head tremor reduction mechanism 29 is located on the frame arms 20, no fastening, tightening or adjustment of a head band is required. It is known that while the variation in the head circumference is appreciable, the length of the frame arms of eyeglasses does not vary significantly. In order to reduce the weight of the head tremor reduction mechanism 29, lightweight but durable materials such as aluminum and plastic can be used to make at least part of the device.

FIG. 1 illustrates a top view of the head of a person wearing a head-tremor reduction frame, according to an embodiment of the present invention. As seen in FIG. 1, the head 500 has two head sides 502 including ears 504. The head tremor reduction device or frame 10 has two frame arms 20 arranged to be put on top of the ears. Each of the frame arms 20 has a mechanical flap 26 arranged to apply a pressuring force behind the ear 504.

Figure 2:
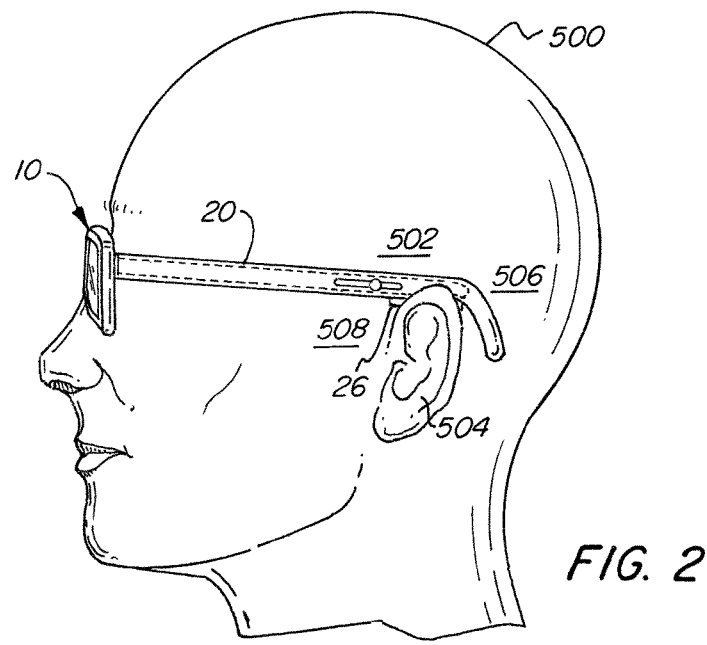
FIG. 2 illustrates a side view of the head of the person as shown in FIG. 1.

FIG. 2 illustrates a side view of the head of the person as shown in FIG. 1. As shown in FIG. 2, the ear 504 has an ear front side 508 and an ear rear side 506. While the mechanical flap 26 is located about the ear center-rear side 506, most of the tremor reduction mechanism is located about the ear front side 508.

Figure 3:
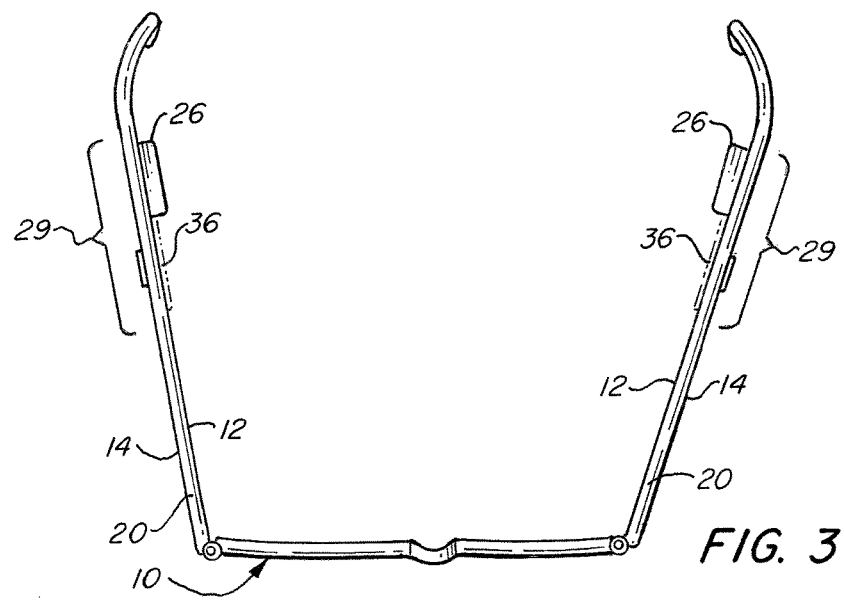
FIG. 3 illustrates a top of the head-tremor reduction frame, according to an embodiment of the present invention.
Figure 4A:
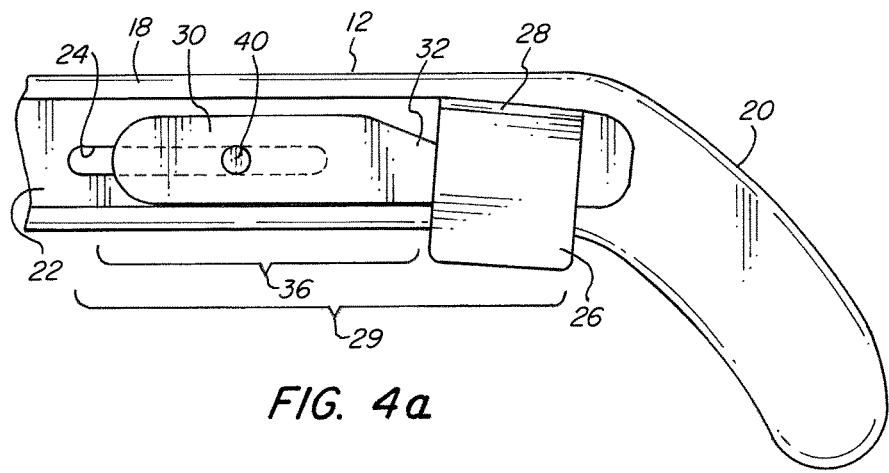
FIG. 4a illustrates the inner side of a frame arm and part of the tremor reduction mechanism, according to an embodiment of the present invention.
Figure 4B:
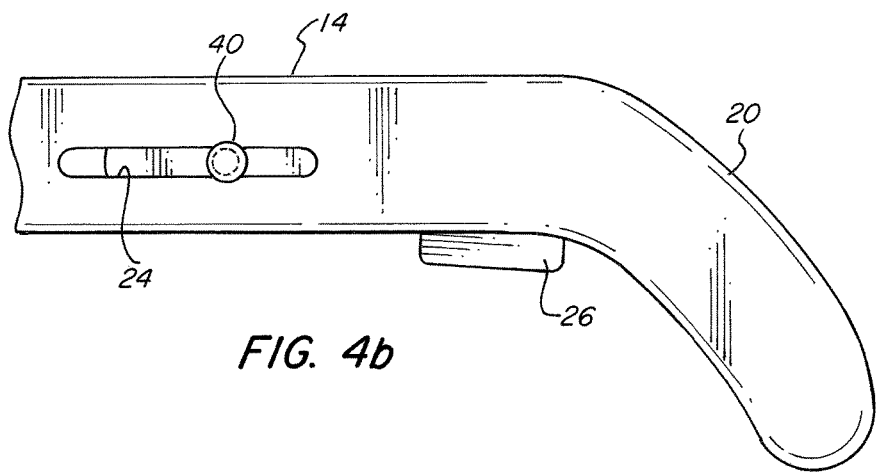
FIG. 4b illustrates the outer side of a frame arm and part of the tremor reduction mechanism, according to an embodiment of the present invention.

FIG. 3 illustrates a top view of the head-tremor reduction frame, according to an embodiment of the present invention. As seen in FIG. 3, the frame 10 has two frame arms 20. Each of the frame arms 20 has an independently adjustable tremor reduction mechanism 29, which includes a mechanical flap 26 and a control section 36. Each of the frame arms has an outer side 14 and an inner side 12 and the mechanical flap 26 is pivotably mounted on the inner side 12 of each of the frame arms 20. As can be seen in FIGS. 4a and 4b, the control sections 36 are mechanically linked to the mechanical flaps 26.

FIG. 4a illustrates the inner side of a frame arm and part of the tremor reduction mechanism, according to an embodiment of the present invention. As seen in FIG. 4a, the tremor reduction mechanism 29 includes a control section 36 and a mechanical flap 26. The control section 36 has a control plate 30 mechanically linked to the mechanical flap 26. The inner side of the frame arm 20 has a frame channel 22 made between two ridges 18, the frame channel 22 dimensioned to accommodate the control plate 30 for movement. The mechanical flap 26 is pivotably attached to the upper ridge 18 with a hinge 28, arranged to apply a pressuring force to the head. The control plate 30 has a tapered end 32 arranged to be located between the mechanical flap 26 and the arm channel 22 to change the pressuring force. The tremor reduction mechanism 29 further comprises a control rod 40 fixedly attached to control plate 30. The frame arm 20 also has a slot 24 located within the frame channel 22. The slot 24 is substantially parallel to the longitudinal axis of the frame arm 20. The slot 24 is dimensioned to receive the control rod 40, allowing the control rod 40 to move along the slot 24 to change the position of the tapered end 32 of the control plate 30 relative to the mechanical flap 26 so as to change the flap angle (see FIG. 5). That the control plate 30 is tapered also helps reduce the shifting force to change the angles of the mechanical flap 26.

FIG. 4b illustrates the outer side of the frame arm 20. The slot 24, the control rod 40 and part of the mechanical flap can be seen in FIG. 4b.

Figure 5:
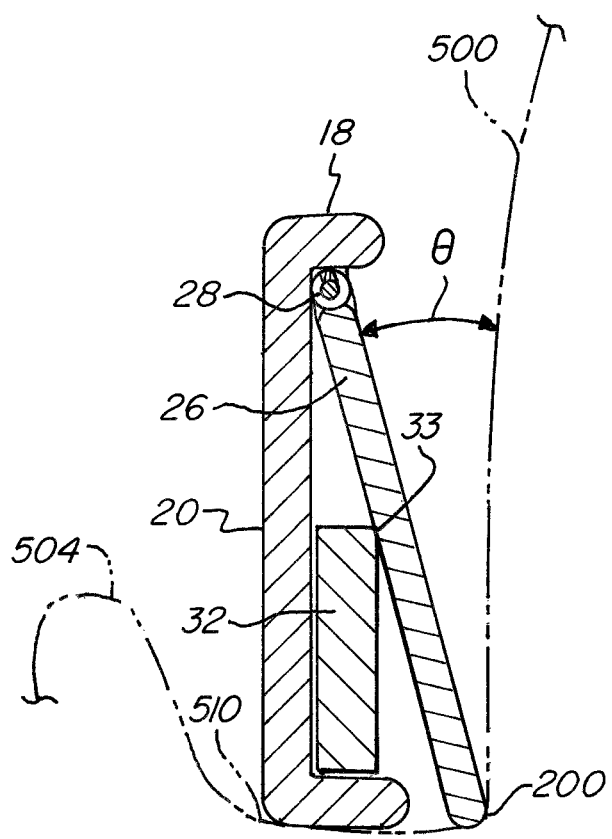

FIG. 5 is a cross sectional view of the frame arm 20 to show the contact between the mechanical flap 26 and the head 500 at a flap-cartilage contact point 200 which is about where the ear 504 is connected to the head by cartilage. As seen in FIG. 5, as the frame arm 20 is placed on top 510 of the ear 504, the pressuring force applied to the head is partly determined by the flap angle θ which can be varied by the contacting point 33 between the mechanical flap 26 and the tapered end 32 of the control plate 30. In an embodiment of the present invention, the mechanical flap 26 is pivotably mounted on or near the upper ridge 18 of the frame arm 20 by a hinge 28. The flap angle θ can be approximately 15 degrees, but it can be smaller or greater, dependent upon the shape of the frame arm 20 and the distance between the frame arm 20 and the head 500. For example, the flap angle θ can be in the range between 10 and 20 degrees. The flap angle θ is adjustable by moving the control plate 30 in the frame channel 22 so as to adjust the pressuring force applied to the head tendons and the muscles behind the ear.

Figure 6:
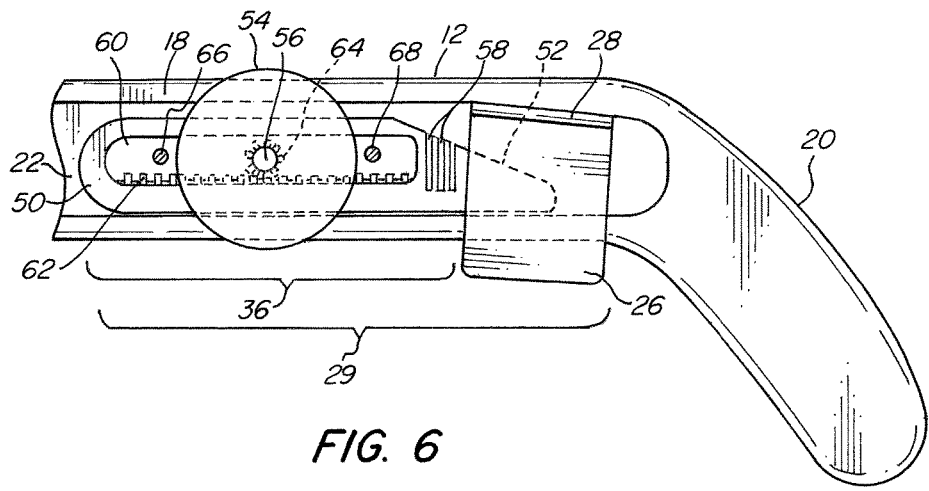
FIG. 6 shows the inner side of a frame arm and part of the tremor reduction mechanism, according to another embodiment of the present invention.
Figure 7:
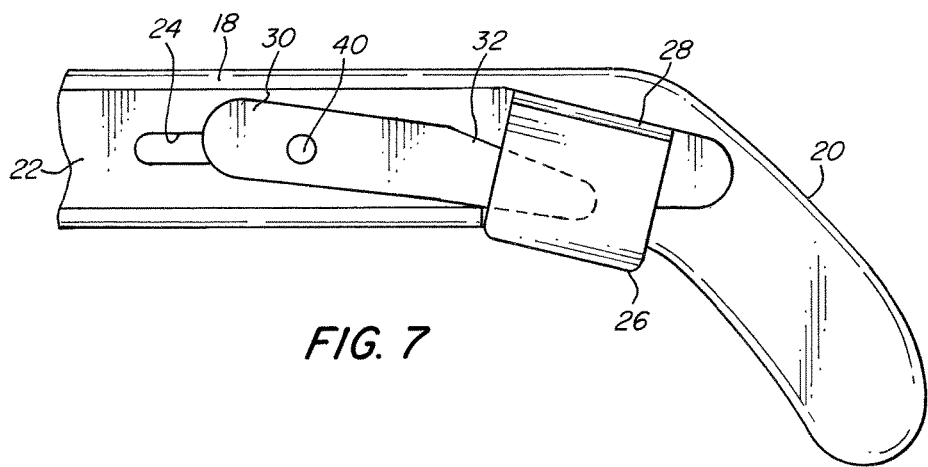
FIG. 7 shows the inner side of a frame arm and part of the tremor reduction mechanism, according to yet another embodiment of the present invention.

FIG. 6 shows the inner side of a frame arm and part of the tremor reduction mechanism, according to another embodiment of the present invention. As seen in FIG. 6, the tremor reduction mechanism 29 includes a control plate 50 having a tapered end 52 arranged to change the flap angle of the mechanical flap 26. The control plate 50 has a plate channel 60 dimensioned to mount a rack 62 and a pinion 64. The rack 62 has a gear bar located on the lower edge of the plate channel 60. The pinion 64 is mounted on a shaft 56. The pinion 64 has a gear wheel movably engaged with the gear bar of the rack 62 for moving the control plate 50 along the frame channel 22 of the frame arm 20. The shaft 56 is attached to a disc 54 for rotation. According to an embodiment of the present invention, a stop 66 and a stop 68 are provided in the frame channel 22 to limit the placement of the control plate 50. In a different embodiment of the present invention, one or both ends of the plate channel 60 can be used as the stops. One or more slits 58 are made on the control plate 50 near the tapered end 52 to render the control plate 50 flexible when the tremor reduction mechanism 29 is mounted on a frame arm that has an end portion curved toward the head (see FIG. 3). In another embodiment of the present invention, the control plate 30 is allowed to be canted about 15 degrees relative to the slot 24 as shown in FIG. 7.

When the mechanical flap 26 and the curve of the frame arm 20 overlap in order to accommodate the positioning of the movable control plate 30 or 50, the frame channel 22 can be widened in the proximity of the mechanical flap 26. The cross section of the tapered end of the control plate 30, 50 can also be shaped to reduce the stress on the flap hinge 28. The contour of the control plate 30, 50 can be designed to reduce the weight of the tremor reduction mechanism 29. Part of the slot 24 can be widened or curved to allow the control plate 30, 50 to be canted (see FIG. 7, for example). The tremor reduction mechanism 29 may have springs and washers to make the movement of the control plate 30, 50 more controllable or smoother.

While the present invention has been described as having two sets of head tremor reduction mechanism 29 separately implemented on two frame arms 20, it is possible to have only one set of head tremor reduction mechanism 29 implemented on one of the frame arms 20. However, using two sets of head tremor reduction mechanism 29 is more effective than using only one set. When the mechanical flap 26 and the curve of the frame arm 20 overlap, the frame channel 22 can be widened to accommodate the control plate 30. Additionally, the slot 24 can be widened or curved downward near the mechanical flap 26 so as to allow the control plate 30 to be canted about 15 degrees, for example. The control plate 30, along with the slot 24, can be curved to accommodate the shape of the head. Furthermore, the flap angle between 10 and 20 degrees appears to be more effective in reducing tremors than increasing flap pressure to the side of the head without controlling the flap angles. A user of the head tremor reduction mechanism 29 should be able to select a flap angle that is more effective in reducing the head tremors. Thus, although the present invention has been described with respect to one or more embodiments thereof, it will be understood by those skilled in the art that the foregoing and various other changes, omissions and deviations in the form and detail thereof may be made without departing from the scope of this invention.

What is claimed is:

1. A device for applying pressure to a part of a head of a person, the head having two opposing head sides, each head side including an ear, each ear having a front side and a rear side, said device comprising:
   a frame mountable on the head, the frame having two frame arms, each frame arm arranged to contact at least a portion of one of the two head sides;
   at least one mechanical flap pivotably mounted on one of the frame arms, the mechanical flap having a flap portion arranged to apply a pressuring force on a head area about the rear side of the ear associated with said one of the two head sides; and
   a control plate having plate end portion with a tapered section to provide a contacting point between the plate end portion and the mechanical flap, wherein the control plate is movable in a movement direction along an arm channel in at least one of the frame arms, so as to change location of the contacting point between the plate end portion and the mechanical flap to adjust the flap angle, and thereby adjust the pressuring force.

2. The device according to claim 1, wherein each of the frame arms has a longitudinal axis, and the movement direction is a direction along the longitudinal axis.

3. The device according to claim 2, wherein the arm channel is provided in a section of the frame arm dimensioned to accommodate the control plate for movement along the movement-direction, said device further comprising a control member arranged to move the control plate along the movement direction.

4. The device according to claim 3, wherein the control member comprises a control rod fixedly attached to the control plate, and wherein said section of the frame arm further comprises a slot dimensioned to receive the control rod, the control rod configured to move to different locations in the slot for locating the control plate to different positions in the arm channel so as to change the location of the contacting point between the plate end portion and the mechanical flap.

5. The device according to claim 4, wherein the slot has a slot axis and the control plate has an upper edge and a lower edge, the lower edge has a cant angle relative to the slot axis such that the lower edge of the control plate near the plate end section is lower than the lower edge near the control rod, and wherein the cant angle is between 0 and 15 degrees.

6. The device according to claim 3, wherein the control plate comprises a plate channel dimensioned to mount a rack having a gear bar and a pinion having a gear wheel movably engaged with the gear bar, and wherein the control member comprises a shaft dimensioned to mount the pinion and a disc attached to the shaft, the disc configured to rotate relative to the plate channel so as to move the control plate to different positions in the arm channel for changing the location of the contacting point between the plate end portion and the mechanical flap.

7. The device according to claim 6, wherein said section of the frame arm further comprises two mechanical stops separately located in the plate channel to limit movement of the control plate in the arm channel.

8. The device according to claim 2, wherein the flap angle is an angle between the mechanical flap and the head area about the rear side of the ear, and wherein the angle is ranged from 10 to 20 degrees.

9. The device according to claim 3, wherein the control plate has one or more slits made thereon near the plate end portion so as to render the control plate flexible near the plate end portion.

10. The device according to claim 1, wherein the frame is an eyeglass frame.

11. A method for reducing head tremor of a person, comprising:
   providing a frame mountable on a head of said person, the head having two opposing head sides, each head side including an ear, the ear having a front side and a rear side, the frame having two frame arms, each frame arm arranged to contact at least a portion of the head side;
   pivotably mounting at least one mechanical flap on one of the frame arms, the mechanical flap having a flap portion arranged to apply a pressuring force on a head area about the rear side of the ear;
   providing an arm channel in a section of the frame arm; and
   providing a control plate having plate end portion with a tapered section to provide a contacting point between the plate end portion and the mechanical flap, wherein the control plate is movable in a movement direction along the arm channel in at least one of the frame arms, so as to change location of the contacting point between the plate end portion and the mechanical flap to adjust the flap angle, and thereby to adjust the pressuring force.

12. The method according to claim 11, wherein each of the frame arms has a longitudinal axis, and the movement direction is a direction along the longitudinal axis.

13. The method according to claim 12, further comprising:
   providing a control member to move the control plate along the movement direction.

14. The method according to claim 13, further comprising:
   fixedly attaching a control rod to the control plate, and
   providing a slot on said section of the frame, the slot dimensioned to receive the control rod, the control rod configured to move to different locations in the slot for locating the control plate to different positions in the arm channel so as to change the location of the contacting point between the plate end portion and the mechanical flap.

15. The method according to claim 14, wherein the slot has a slot axis and the control plate has an upper edge and a lower edge, the lower edge has a cant angle relative to the slot axis such that the lower edge of the control plate near the plate end section is lower than the lower edge near the control rod, and wherein the cant angle is between 0 and 15 degrees.

16. The method according to claim 13, further comprising:
   providing a plate channel on the control plate, the plate channel dimensioned to mount a rack having a gear bar and a pinion having a gear wheel movably engaged with the gear bar, and wherein the control member comprises a shaft dimensioned to mount the pinion and a disc attached to the shaft, the disc configured to rotate relative to the plate channel so as to move the control plate to different positions in the arm channel for changing the location of the contacting point between the plate end portion and the mechanical flap.

17. The method according to claim 16, further comprising:
   providing two mechanical stops separately in the plate channel to limit movement of the control plate in the arm channel.

18. The method according to claim 12, wherein the flap angle is an angle between the mechanical flap and the head area about the rear side of the ear, and wherein the angle is ranged from 10 to 20 degrees.

* * * * *